(12) United States Patent
Tamori et al.

(10) Patent No.: US 7,732,051 B2
(45) Date of Patent: Jun. 8, 2010

(54) POLYMER-COATED MAGNETIC PARTICLES COMPRISING A 2,3-HYDROXYPROPYL GROUP, AND PROBE-BONDED PARTICLES

(75) Inventors: Kouji Tamori, Tsuchiura (JP); Eiji Takamoto, Tsuchiura (JP); Masaru Ueno, Tsukuba (JP); Tetsuo Fukuta, Tsuchiura (JP); Tomohiro Uetsuhara, Tsukuba (JP); Mitsuhiro Murata, Ushiku (JP)

(73) Assignee: JSR Corporation, Tokyo (JP)

( * ) Notice: Subject to any disclaimer, the term of this patent is extended or adjusted under 35 U.S.C. 154(b) by 400 days.

(21) Appl. No.: 11/772,616

(22) Filed: Jul. 2, 2007

(65) Prior Publication Data

US 2008/0026222 A1    Jan. 31, 2008

(30) Foreign Application Priority Data

Jul. 26, 2006    (JP) .............................. 2006-203044

(51) Int. Cl.
 *B32B 5/16*    (2006.01)
(52) U.S. Cl. ...................................... 428/407; 525/902
(58) Field of Classification Search ................ 428/403, 428/407; 525/902
See application file for complete search history.

(56) References Cited

U.S. PATENT DOCUMENTS

| | | | |
|---|---|---|---|
| 4,336,173 | A | 6/1982 | Ugelstad |
| 4,459,378 | A | 7/1984 | Ugelstad |
| 5,583,056 | A * | 12/1996 | Brouwer ..................... 436/525 |
| 5,635,405 | A * | 6/1997 | Brouwer ..................... 436/525 |
| 5,834,121 | A * | 11/1998 | Sucholeiki et al. .......... 428/407 |
| 2007/0060671 | A1 | 3/2007 | Sugano et al. |
| 2007/0099814 | A1 * | 5/2007 | Tamori et al. ............... 510/446 |

FOREIGN PATENT DOCUMENTS

| | | |
|---|---|---|
| EP | 1 108 743 A2 | 6/2001 |
| EP | 1 348 731 A1 | 10/2003 |
| EP | 1 780 544 A1 | 5/2007 |
| JP | 57-24369 | 5/1982 |
| JP | 61-215602 | 9/1986 |
| JP | 61-215603 | 9/1986 |
| JP | 61-215604 | 9/1986 |
| JP | 2-501753 | 6/1990 |
| JP | 10-505118 | 5/1998 |
| JP | 2005-069926 | * 3/2005 |

(Continued)

OTHER PUBLICATIONS

U.S. Appl. No. 12/602,138, filed Nov. 27, 2009, Tamori, et al.

(Continued)

*Primary Examiner*—H. (Holly) T Le
(74) *Attorney, Agent, or Firm*—Oblon, Spivak, McClelland, Maier & Neustadt, L.L.P.

(57) ABSTRACT

A method for producing magnetic particles includes forming a hydrophobic first polymer layer on the surface of a mother particle containing superparamagnetic particles, forming a second polymer layer having glycidyl groups at least on its surface on the first polymer layer, and introducing a polar group containing one or more of at least one atom selected from the group consisting of an oxygen atom, a nitrogen atom, and a sulfur atom by chemically modifying the glycidyl groups.

16 Claims, 1 Drawing Sheet

FOREIGN PATENT DOCUMENTS

| | | |
|---|---|---|
| JP | 2005-83904 | 3/2005 |
| JP | 2005-83905 | 3/2005 |
| JP | 3738847 | 11/2005 |
| JP | 2006-511935 | 4/2006 |
| JP | 2006-131771 * | 5/2006 |
| WO | WO 2004/053490 A1 | 6/2004 |
| WO | WO 2005/042622 A1 | 5/2005 |

OTHER PUBLICATIONS

U.S. Appl. No. 11/914,986, filed Nov. 20, 2007, Takahashi, et al.
U.S. Appl. No. 11/961,562, filed Dec. 20, 2007, Tamori, et al.
Jana Krizova, et al., "Magnetic hydrophilic methacrylate-based polymer microspheres for genomic DNA isolation", Journal of Chromatography, XP005003950, vol. 1064, No. 2, Feb. 4, 2005, pp. 247-253.
U.S. Appl. No. 12/529,824, filed Sep. 3, 2009, Katayose, et al.
U.S. Appl. No. 11/954,289, filed Dec. 12, 2007, Tamori, et al.

* cited by examiner

POLYMER-COATED MAGNETIC PARTICLES COMPRISING A 2,3-HYDROXYPROPYL GROUP, AND PROBE-BONDED PARTICLES

Japanese Patent Application No. 2006-203044 filed on Jul. 26, 2006 is hereby incorporated by reference in its entirety.

BACKGROUND OF THE INVENTION

The present invention relates to magnetic particles, a method for producing the same, and probe-bonded particles.

Since magnetic particles can be easily applied to washing of materials by magnetic separation and can provide an outstanding reaction field in the researches of antigen-antibody immunoreactions, hybridization of DNAs or DNA and RNA, interactions of pharmaceutical candidate substances and in vivo substances, and the like, the magnetic particles are being actively used in the biochemical field, particularly in the research of diagnostic agents and pharmaceuticals in recent years.

Particularly as biochemical carrier particles, polystyrene particles are mainly used for physical adsorption sensitization, and polystyrene particles modified with a carboxyl group are mainly used for chemical bond sensitization. However, these particles adsorb a large amount of physiologically active substances existing in test samples such as cells, proteins, and DNAs which are not the target substances. Such adsorption of non-target substances is herein referred to as "non-specific adsorption". The non-specific adsorption hinders performance of sensitization particles. That is, the non-specific adsorption has been a serious hindrance when using these particles.

As a biochemical carrier exhibiting only small non-specific adsorption, gels based on sugar chains such as agarose and sepharose are used. These gels, however, tend to reduce the activity of bonded probes and cannot emit a sufficient number of signals in many cases.

Reducing non-specific adsorption is also demanded for magnetic particles. To this end, magnetic particles with glycidyl groups introduced onto the particle surface have been proposed. For example, JP-A-2006-131771 proposes a method of dispersing superparamagnetic particles in styrene and glycidyl methacrylate and polymerizing while finely dispersing the mixture by supersonic treatment. However, not only this method cannot sufficiently cover magnetic materials with glycidyl methacrylate to adequately reduce the non-specific adsorption, but also the average diameter of the resulting particles is 200 nm or less, which is too small for the particles to exhibit sufficient magnetic separation performance.

The applicant of this invention has disclosed a method for manufacturing magnetic particles comprising a step of providing a two layer polymer coat in order to efficiently produce particles for diagnostic agents having a uniform diameter and being free from release of magnetic materials or elution of substances originating from magnetic material components such as iron ion (Japanese Patent No. 3738847). The applicant further disclosed magnetic particles with reduced non-specific adsorption (JP-A-2005-83904 and JP-A-2005-83905). However, further reduction of non-specific adsorption is desired.

Although the objective is not necessarily reducing the non-specific adsorption, JP-T-2-501753, for example, discloses a method for producing magnetic particles with glycidyl groups introduced therein by polymerizing a mixture of a magnetic material and a monomer in the presence of nuclear particles, and coating the resulting polymer. However, since only a very small amount of the mixture of the magnetic material and the monomer polymerize on the nuclear particles, only a very small amount of magnetic materials can be incorporated into the nuclear particles. The product thus exhibits poor magnetic separation properties.

JP-T-10-505118 discloses a reaction for introducing amino groups into magnetic particles with glycidyl groups introduced therein. The resulting magnetic particles are porous particles to be used for an ion-exchange purposes having remarkable non-specific adsorption.

JP-T-2006-511935 proposes a method of causing a magnetic material to deposit on the surface and inside of particles and coating the particles with a polymer having glycidyl groups. However, according to this method, when magnetic particles are caused to deposit on the particle surface, the polymer having glycidyl groups can be coated only insufficiently, failing to reduce the non-specific adsorption.

SUMMARY

The invention relates to magnetic particles exhibiting only a small degree of non-specific adsorption of proteins, nucleic acids, and the like, and having remarkably high sensitivity and low noise, particularly in the field of biochemical and pharmaceutical products, to a method for producing the magnetic particles, and to probe-bonded particles.

In order to attain the above objective, the inventors have conducted extensive studies and found that magnetic particles exhibiting remarkably high sensitivity and low noise in the field of biochemical and pharmaceutical products can be obtained by polymerizing a coating layer having glycidyl groups on the outermost layer and chemically modifying the glycidyl groups. This finding has led to the completion of the invention. According to the invention, magnetic particles and a method for producing the same according to the following aspects can be provided.

A method for producing magnetic particles according to a first aspect of the invention comprises:

forming a hydrophobic first polymer layer on the surface of a mother particle containing superparamagnetic particles;

forming a second polymer layer having glycidyl groups at least on its surface on the first polymer layer; and introducing a polar group containing one or more of at least one atom selected from the group consisting of an oxygen atom, a nitrogen atom, and a sulfur atom by chemically modifying the glycidyl groups.

In the above method for producing magnetic particles, the chemical modification of the glycidyl groups may include a reaction of introducing an amino group.

In the above method for producing magnetic particles, the chemical modification of the glycidyl groups may include a reaction of introducing an aldehyde group.

In the above method for producing magnetic particles, the chemical modification of the glycidyl groups may include a reaction of introducing a carboxyl group.

In the above method for producing magnetic particles, the chemical modification of the glycidyl groups may further include a reaction of converting the carboxyl group into an active ester group.

In the above method for producing magnetic particles, the chemical modification of the glycidyl groups may further include a reaction of converting the carboxyl group into an active ester group.

In the method for producing magnetic particles according to a second aspect of the invention, the mother particle comprises a nuclear particle and a magnetic material layer containing superparamagnetic particles formed on the surface of the nuclear particle; and the first polymer layer is formed on the magnetic material layer.

A magnetic particle according to a third aspect of the invention comprises:

a mother particle containing superparamagnetic particles;

a hydrophobic first polymer layer formed on the surface of the mother particle; and a second polymer layer having an amino group and a 2,3-hydroxypropyl group formed on the first polymer layer.

A magnetic particle according to a fourth aspect of the invention comprises:

a mother particle containing superparamagnetic particles;

a hydrophobic first polymer layer formed on the surface of the mother particle; and a second polymer layer having an aldehyde group and a 2,3-hydroxypropyl group formed on the first polymer layer.

A magnetic particle according to a fifth aspect of the invention comprises:

a mother particle containing superparamagnetic particles;

a hydrophobic first polymer layer formed on the surface of the mother particle; and a second polymer layer having a carboxyl group and a 2,3-hydroxypropyl group formed on the first polymer layer.

A magnetic particle according to a sixth aspect of the invention comprises:

a mother particle containing superparamagnetic particles;

a hydrophobic first polymer layer formed on the surface of the mother particle; and a second polymer layer having an active ester group and a 2,3-hydroxypropyl group formed on the first polymer layer.

In the above magnetic particle, the mother particle may comprise a nuclear particle and a magnetic material layer containing the superparamagnetic particles formed on the surface of the nuclear particle; and the first polymer layer may be formed on the magnetic material layer.

The magnetic particle may be used for probe bonding.

A probe-bonded particle according to a seventh aspect of the invention comprises the above magnetic particle and a probe bonded to the magnetic particle.

The above magnetic particles exhibit remarkably high sensitivity and low noise in the field of biochemical and pharmaceutical products and can provide a high S/N ratio in biochemical inspections due to a small non-specific adsorption of proteins, nucleic acids, and the like.

According to the method for producing magnetic particles of the invention, magnetic particles exhibiting only a small degree of non-specific adsorption of proteins, nucleic acids, and the like, and having a remarkably high sensitivity and low noise, particularly in the field of biochemical and pharmaceutical products, can be efficiently produced.

The above probe-bonded particles exhibit only small probe dissociation and small non-specific adsorption, and high sensitivity.

DETAILED DESCRIPTION OF THE EMBODIMENT

Figure 1:
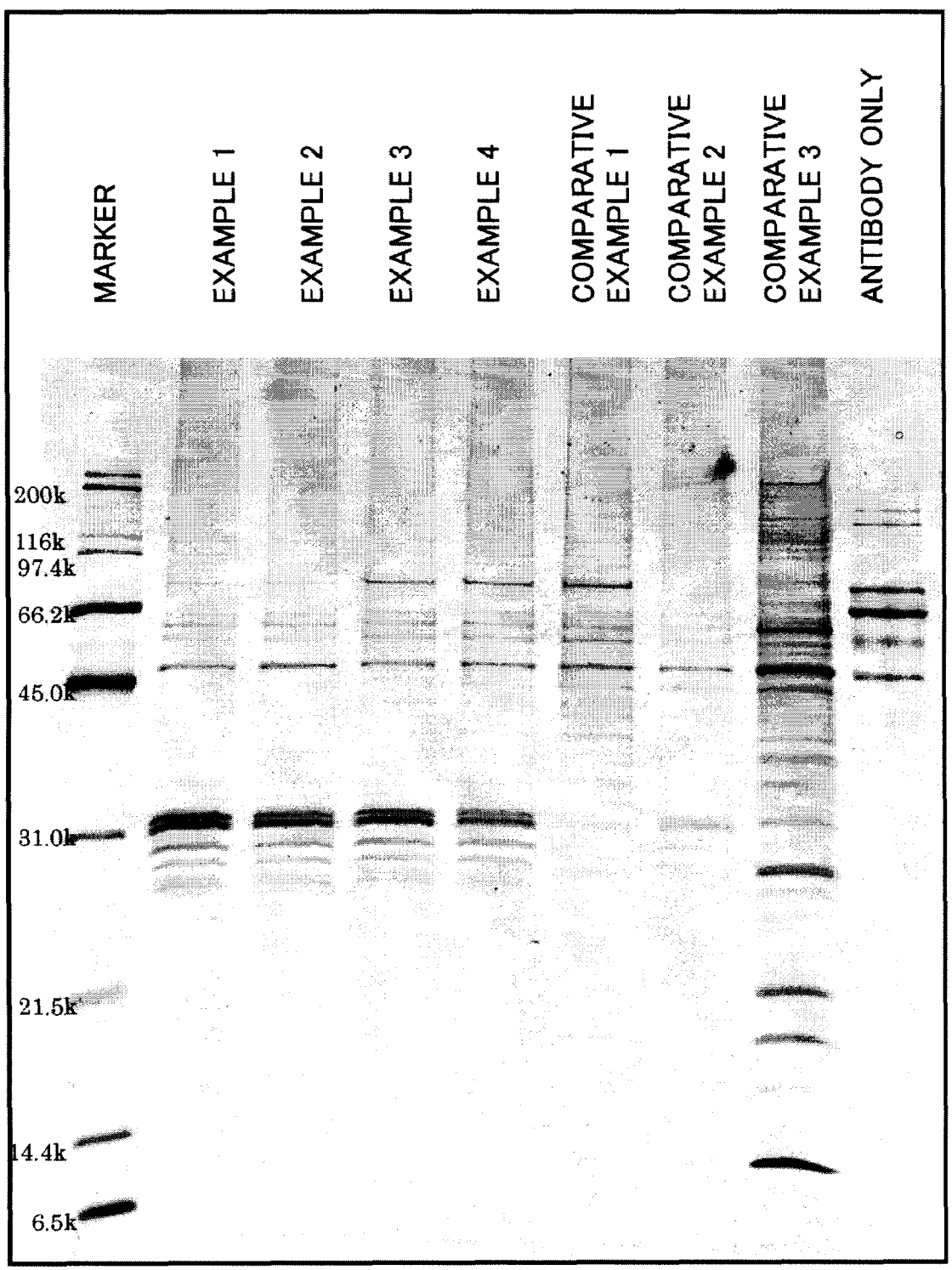
FIG. 1 shows an electrophoresis pattern showing non-specific adsorption and sensitivity of probe-bonded particles obtained in Examples 1 to 4.

The magnetic particles, the method for producing the same, and the probe-bonded particles according to one embodiment of the invention are described below.

1. Magnetic Particles And Method For Producing Same

The method for producing magnetic particles according to one embodiment of the invention comprises forming a hydrophobic first polymer layer on the surface of a mother particle containing superparamagnetic particles, forming a second polymer layer having glycidyl groups at least on its surface on the first polymer layer, and introducing a polar group containing one or more of at least one atom selected from the group consisting of an oxygen atom, a nitrogen atom, and a sulfur atom by chemically modifying the glycidyl groups.

1.1. Mother Particles

As the form of the mother particles, for example, (I) particles having superparamagnetic particles dispersed in a continuous phase of a non-magnetic material such as an organic polymer, (II) particles formed of a secondary aggregate of superparamagnetic particles as a core and a non-magnetic material such as an organic polymer as a shell, and (III) particles containing a nuclear particle of a non-magnetic material such as an organic polymer and a secondary aggregate layer (magnetic material layer) of superparamagnetic particles provided on the surface of the nuclear particle can be given. Among these, the mother particles (III) in which the magnetic material layer containing superparamagnetic particles is formed on the nuclear particle are preferable due to the excellent magnetic response and capability of uniformly controlling the particle diameter. The configuration of the mother particles (III) is described below.

1.1.1. Nuclear Particles

The nuclear particles are basically made from a nonmagnetic substance which can be either an organic substance or an inorganic substance. A specific material is suitably selected according to the purpose of use and the like of diagnostic particles. Polymers can be given as a typical organic material. As the polymer, vinyl polymers are preferable, with crosslinked polystyrene and crosslinked polymethyl methacrylate being most preferable polymers. These polymers may have a functional group such as a carboxyl group introduced therein.

The average particle diameter of the nuclear particles is preferably from 0.4 to 200 micrometers, more preferably from 0.8 to 100 micrometers, and most preferably from 1.0 to 50 micrometers. If the average particle diameter of the nuclear particles is less than 0.4 micrometers, magnetic separation properties may be poor. On the other hand, if the average particle diameter of the nuclear particles is more than 200 micrometers, gravity precipitation is remarkable, which may produce probe-bonded particles with a non-uniform reaction field.

An organic substance such as a polymer is preferable as the material for the nuclear particles from the viewpoint of processability when preparing a complex and the lightweight property of a polymer. The average particle diameter in the invention is determined by measuring the diameters of particles by a laser diffraction particle size distribution measuring device.

The polymer particles as the nuclear particles having the average particle diameter of the specific range mentioned above can be obtained by, for example, suspension polymerization of vinyl monomers or pulverization of a bulk polymer.

The nuclear polymer particles having a uniform particle diameter can be easily prepared by the swelling polymerization method described in JP-B-57-24369 and the polymerization methods previously proposed by the applicant of the invention (JP-A-61-215602, JP-A-61-215603, and JP-A-61-215604)

1.1.2. Superparamagnetic Particles

Typical superparamagnetic particles are fine particles of iron oxide with a particle diameter of 20 nm or less (preferably from 5 to 20 nm) and include ferrite represented by the formula $MnFe_2O_4$ (Mn=Co, Ni, Mg, Cu, $Li_{0.5}Fe_{0.5}$, etc.), magnetite represented by $Fe_3O_4$, and gamma-$Fe_2O_3$. Superparamagnetic particles containing either one of gamma-$Fe_2O_3$ or $Fe_3O_4$ with strong saturated magnetization and small residual magnetization are preferable.

The ratio of the nuclear particles to the superparamagnetic particles is preferably from 95:5 to 20:80. If the amount of the superparamagnetic particles is less than this range, the magnetic separation properties may be poor. An amount of the superparamagnetic particles more than this range may result in superparamagnetic particles which are not made into a complex due to too large a number of superparamagnetic particles per nuclear particle.

Superparamagnetic particles with a hydrophobic surface are preferable in order to increase affinity and mutual solubility of the nuclear particles and monomers used in the following steps. The method described in Japanese Patent No. 3738847 can be given as a method for hydrophobicizing the surface of magnetic fine particles. Such superparamagnetic particles can also be obtained by causing particles to deposit from and washing with a known magnetic fluid using a suitable poor solvent.

1.1.3. Mother Particles with Magnetic Material Layer Formed Thereon

As the method for forming a magnetic material layer containing superparamagnetic particles on the surfaces of the mother particles, a method of mixing nuclear particles with superparamagnetic particles to cause the superparamagnetic particles to be physically adsorbed on the surface of the nuclear particles is preferable. To be "physically adsorbed" indicates a method of adsorbing or bonding without an accompanying chemical reaction. As a method for causing superparamagnetic particles to be adsorbed on the surface of nuclear particles, for example, a method of dry blending of nuclear particles and superparamagnetic particles and physically applying a strong force from the outside to produce a complex of the nuclear particles and the superparamagnetic particles can be given. As the method for physically applying a strong force from the outside, for example, a method of using a mortar, an automatic mortar, or a ball mill, a blade pressure fine particle compressing method, a method of using a mechanochemical effect such as a mechanofusion method, and an impact method in a high-speed flow using a jet mill, a hybridizer, or the like can be given. Use of a high physical adsorption force is desirable in order to efficiently obtain a firmly bonded complex. In order to produce a complex with a strong physical adsorption force, a method of producing the complex in a vessel equipped with a stirrer while rotating the stirrer at a stirring blade peripheral velocity of 15 m/sec or more, more preferably 30 m/sec or more, and still more preferably 40 to 150 m/sec can be given. If the stirring blade peripheral velocity is less than 15 m/sec, sufficient energy for causing superparamagnetic particles to be adsorbed on the surfaces of the nuclear particles may not be obtained. Although the upper limit of the peripheral velocity of the stirring blade is not particularly limited, such an upper limit is naturally determined according to the apparatus used, energy efficiency, and the like.

1.2. Hydrophobic First Polymer Layer

Next, the configuration and method of forming the hydrophobic first polymer layer formed on the surfaces of the mother particles (hereinafter referred to from time to time as "the hydrophobic first polymer layer") are described.

Monomers for forming the hydrophobic first polymer layer (hereinafter referred to from time to time as "the first monomer part") contain 80 wt % or more, preferably 95 wt % or more, and more preferably 98 wt % or more of hydrophobic monomers. If the amount of the hydrophobic monomers in the first monomer part is less than 80 wt %, non-specific adsorption may be worsened. The hydrophobic monomer is a polymerizable monomer or a mixture of polymerizable monomers with water solubility of 2.5 wt % at 25° C. The hydrophobic monomer may be a mono-functional (non-crosslinkable) monomer, a crosslinkable monomer, or a mixture of the mono-functional monomer and a crosslinkable monomer.

The first polymer layer can be formed by polymerizing the first monomer part which contains 80 wt % or more of hydrophobic monomers as a main raw material in a liquid containing, as required, side raw materials such as an initiator, an emulsifying agent, a dispersant, an electrolyte, a crosslinking agent, and a molecular-weight modifier in the presence of mother particles. A magnetic material layer can be effectively covered and non-specific adsorption can be effectively reduced by forming the first polymer layer by polymerization in this manner.

As examples of the mono-functional monomers among the hydrophobic monomers which can be used for the first monomer part, aromatic vinyl monomers such as styrene, alpha-methylstyrene, and halogenated styrene, and ethylenically-unsaturated carboxylic acid alkyl esters such as methyl acrylate, ethyl acrylate, ethyl methacrylate, stearyl acrylate, stearyl methacrylate, cyclohexyl acrylate, cyclohexyl methacrylate, iso-bornyl acrylate, and iso-bornyl methacrylate can be given. As examples of the crosslinkable monomers among the hydrophobic monomers, poly-functional (meth)acrylates such as ethylene glycol diacrylate, ethylene glycol dimethacrylate, trimethylolpropane triacylate, trimethylolpropane trimethacrylate, pentaerythritol triacylate, pentaerythritol trimethacrylate, dipentaerythritol hexaacrylate, and dipentaerythritol hexamethacrylate; conjugated diolefins such as butadiene and isoprene; divinylbenzene, diallylphthalate, allyl acrylate, and allyl methacrylate can be given.

The first monomer part may contain less than 20 wt % of non-hydrophobic monomers (hydrophilic monomers). As examples of the mono-functional monomers among the non-hydrophobic monomers, monomers having a carboxyl group such as acrylic acid, methacrylic acid, maleic acid, and itaconic acid; (meth)acrylates having a hydrophilic functional group (for example, a hydroxyl group, an amino group, and an alkoxy group) such as 2-hydroxyethyl acrylate, 2-hydroxyethyl methacrylate, glycerol acrylate, glycerol methacrylate, methoxyethyl acrylate, methoxyethyl methacrylate, polyethylene glycol acrylate, polyethylene glycol methacrylate, 2-dimethylaminoethyl (meth)acrylate, 2-diethylaminoethyl (meth)acrylate, 2-dimethylaminopropyl (meth)acrylate, and 3-dimethylaminopropyl(meth)acrylate; acrylamide, methacrylamide, N-methylolacrylamide, N-methylolmethacrylamide, diacetoneacrylamide, N-(2-diethylaminoethyl)(meth) acrylamide, N-(2-dimethylaminopropyl)(meth)acrylamide, and N-(3-dimethylaminopropyl)(meth)acrylamide can be given. As examples of the crosslinkable monomers among the non-hydrophobic monomers, hydrophilic monomers such as polyethylene glycol diacrylate, polyethylene glycol dimethacrylate, and poly(meth)acrylic ester of polyvinyl alcohol can be given. The amount of the non-hydrophobic monomer contained in the first monomer part is less than 20 wt %, preferably less than 5 wt %, and more preferably less than 2 wt %.

The amount of the crosslinkable monomers (the total of the hydrophobic monomers and the non-hydrophobic monomers) in the first monomer part is preferably from 1 to 40 wt %, and more preferably from 5 to 20 wt %, of 100 wt % of the monomers forming the first polymer layer. If the amount of the crosslinkable monomers in the first monomer part is more than 40 wt %, the particles may become porous and non-specific adsorption may be increased.

As the initiator, an oil-soluble initiator is more preferable when the initiators are classified according to solubility in water. When a water-soluble initiator is used, a large amount of new particles formed only from hydrophobic monomers which do not contain magnetic material-coated particles tend to be produced instead of polymerization on the composite particle surface.

As examples of the oil-soluble initiator, peroxides and azo compounds such as benzoyl peroxide, lauroyl peroxide, tert-butylperoxy 2-ethylhexanoate, 3,5,5-trimethylhexanoyl peroxide, and azobisisobutyronitrile can be given.

As the water-soluble initiator, persulfates such as potassium persulfate, ammonium persulfate, and sodium persulfate; hydrogen peroxide, mineral acid salt of 2,2-azobis(2-aminopropane), and azobiscyanovaleric acid and the alkaline metal salt and ammonium salt thereof can be given. Redox initiators which are combinations of a persulfate or a hydrogen peroxide salt with sodium hydrogen sulfite, sodium thiosulfate, ferrous chloride, or the like can also be given. Persulfate is particularly suitably used. These initiators are used in an amount preferably of 0.01 to 8 wt % of the total amount of monomers.

As an emulsifying agent, a commonly used anionic surfactant or nonionic surfactant can be used independently or in combination of two or more. As examples of the anionic surfactant, in addition to anionic surfactants such as an alkali metal salt of a higher alcohol sulfate, an alkali metal salt of alkylbenzenesulfonic acid, an alkali metal salt of dialkyl succinate sulfonic acid, an alkali metal salt of alkyl diphenyl ether disulfonic acid, a sulfate salt of polyoxyethylene alkyl (or alkylphenyl)ether, a phosphate salt of polyoxyethylene alkyl (or alkylphenyl)ether, and a formalin condensate of sodium naphthalenesulfonate, reactive emulsifying agents such as Eleminol JS-2™, Eleminol JS-5™ (manufactured by Sanyo Chemical Industries, Ltd.), Latemul S-120™, Latemul S-180A™, Latemul S-180™, Latemul PD-104™ (manufactured by Kao Corp.), Aquaron HS-10™, Aquaron HS-20™, Aquaron KH-10™ (manufactured by Daiichi Kogyo Seiyaku Co., Ltd.), and Adecalia Soap SE-10N™, Adecalia Soap SR-10™ (manufactured by Asahi Denka Kogyo Co., Ltd.) can be given.

As examples of the nonionic surfactant, in addition to polyoxyethylene alkyl ether, polyoxyethylene alkyl phenyl ether, and the like, reactive nonionic surfactants such as Aquaron RS-20™ (manufactured by Daiichi Kogyo Seiyaku Co., Ltd.) and Adekalia Soap NE-20™ (manufactured by Asahi Denka Kogyo Co., Ltd.) can be given.

The method of addition of monomers to the polymerization system for forming the first polymer layer is not specifically limited. Any one of the methods among a method of adding monomers at one time, a method of adding monomers in portions, or a method of continuously adding monomers may be used. Although the polymerization temperature varies according to the initiators, the monomers are polymerized at a temperature usually from 10 to 90° C., and preferably from 30 to 85° C., usually for 1 to 30 hours.

The thickness of the first polymer layer is preferably from 0.005 to 20 micrometers, and more preferably from 0.01 to 5 micrometers. It is preferable that the first polymer layer completely covers the magnetic material layer.

In the magnetic particles according to this embodiment, leakage of the superparamagnetic particles can be prevented by forming the first monomer layer on the surface of the mother particle. Particularly, in the magnetic particles according to this embodiment, when the mother particles contain a nuclear particle and a magnetic material layer containing superparamagnetic particles formed on the surface of the nuclear particle, leakage of the superparamagnetic particles can be effectively prevented due to the first monomer layer formed on the surface of the mother particle.

1.3. Second Polymer Layer Having Glycidyl Groups

Next, the configuration and method of forming the second polymer layer having glycidyl groups (hereinafter referred to from time to time as "the second polymer layer") formed on the surface of the first polymer layer are described.

A major object of the second polymer layer is to introduce a functional group for forming the particle surface with a low non-specific adsorption property. The particle surface with a low non-specific adsorption property is suitable, for example, as the surfaces of the magnetic particles for probe bonding.

Monomers for forming the second polymer layer (hereinafter referred to from time to time as "the second monomer part") contains 20 wt % or more, preferably 40 wt % or more, and more preferably 80 wt % or more of glycidyl group-containing monomers. As other monomers for forming the second polymer layer, the monomers given as monomers used for forming the first monomer part can be used. A second polymer layer having two or more glycidyl groups can be obtained by polymerizing a second monomer part containing a predetermined amount of glycidyl group-containing monomers. The number of glycidyl groups contained in the second polymer layer is usually two or more.

The second polymer layer can be formed by basically the same method as the method for forming the first polymer layer. That is, the second polymer layer can be formed by polymerizing the second monomer part which is a main raw material in a liquid containing, as required, side raw materials such as an initiator, an emulsifying agent, a dispersant, an electrolyte, a crosslinking agent, and a molecular-weight modifier in the presence of particles in which the first polymer layer is formed.

As copopolymerizable monomers containing a glycidyl group, glycidyl acrylate, glycidyl methacrylate, allyl glycidyl ether, and the like can be given.

It is preferable that the second polymer part further contain crosslinkable monomers in an amount preferably from 1 to 40 wt %, and more preferably from 5 to 20 wt %, of 100 wt % of the monomers forming the second polymer part. If the amount of the crosslinkable monomers in the second monomer part is more than 40 wt %, the particles may become porous and non-specific adsorption may be increased.

The method of adding monomers to the polymerization system for forming the second polymer layer is not specifically limited. Any one of methods of adding all monomers at one time, a method of adding the monomers in portions, or a method of continuously adding the monomers may be used. Although the polymerization temperature varies according to the initiators, the monomers are polymerized at a temperature usually from 10 to 90° C., and preferably from 30 to 85° C., for usually 1 to 30 hours.

The thickness of the second polymer layer is preferably from 0.005 to 5 micrometers, and more preferably from 0.005 to 1 micrometer.

1.4. Chemical Modification of Glycidyl Groups

The following reactions, for example, may be included in chemical modification of the glycidyl groups of the second polymer layer. Two or more of these reactions may be combined.

(a) Reaction of introducing an amino group
(b) Reaction of introducing an aldehyde group
(c)-1 Reaction of introducing a carboxyl group
(c)-2 Reaction of converting the introduced carboxyl group into an active ester group A polar group containing one or more atoms selected from the group consisting of an oxygen atom, a nitrogen atom, and a sulfur atom can be introduced by chemical modification of the glycidyl groups of the second polymer layer. The polar group is preferably a functional group reactive with a probe, for example, at least one group selected from an amino group, an aldehyde group, a carboxyl group, and an active ester group. For example, when the second polymer layer of the resulting magnetic particles has the above-mentioned polar group and a 2,3-hydroxypropyl group mentioned later, the magnetic particles have excellent capability of bonding with a probe and exhibit only a small non-specific adsorption.

Each of the above reactions is described below.

1.4.1. Reaction for Introducing Amino Group (a) The reaction for introducing an amino group is more specifically a reaction to introduce an amino group to the second polymer layer by causing an amination agent to act on the particles on which the second polymer layer having a glycidyl group has been formed. Magnetic particles having an amino group introduced therein can be obtained by this reaction. The magnetic particles having an amino group introduced therein can be suitably used for bonding a probe.

As an amination agent, an organic compound having two or more amino groups in the molecule is preferable. As examples, ammonia, organic compounds having two amino groups in the molecule (diamines), and organic compounds having three or more amino groups in the molecule (polyamines) can be given.

As examples of the diamine, primary diamines such as ethylenediamine, propylenediamine, and o-phenylenediamine can be given. As examples of the organic compound having three or more amino groups in the molecule, 1,2,3-triaminopropane, tetra(aminomethyl)methane, 1,3,5-triaminobenzene, and 1,2,3,4-tetraaminobenzene can be given.

The reaction for introducing amino groups is carried out by dispersing dry particles in an amination agent as is or by using particles dispersed in an aqueous solvent. An aqueous solvent is a mixed solvent of a water-soluble organic solvent and water, or water. As examples of the water-soluble organic solvent, methanol, ethanol, acetone, and dimethylformamide can be given. A preferable temperature of the reaction to introduce amino groups and the reaction time vary according to the concentration of glycidyl groups in the second polymer layer, the presence or absence of a solvent, the type of the solvent, and the like. The reaction is carried out at a temperature usually from 4° C. to 100° C., preferably from 20° C. to 80° C., usually for 10 minutes to 48 hours, and preferably for 1 hour to 24 hours. It is not necessary that all glycidyl groups be aminated in the reaction for introducing amino groups.

The amount of the amino groups in the magnetic particles according to this embodiment is preferably from 0.1 micromol/g to 100 micromol/g, and still more preferably from 0.5 micromol/g to 50 micromol/g. If the amount of the amino groups is less than 0.1 micromol/g, the number of probes that can bond to the magnetic particles may be too small resulting in weak signal, and if more than 100 micromol/g, the non-specific adsorption may increase.

It is possible to hydrolyze a part of two or more glycidyl groups before introducing amino groups. It is also possible to hydrolyze a part of two or more glycidyl groups during the reaction of introducing amino groups. In addition, it is possible to hydrolyze all or a part of two or more glycidyl groups remaining after the reaction of introducing amino groups.

2,3-Dihydroxypropyl groups are generated by hydrolyzing glycidyl groups. The second polymer layer possessing 2,3-dihydroxypropyl groups exhibits reduced non-specific adsorption. Glycidyl groups can be hydrolyzed using a suitable acid catalyst or a base catalyst, for example, in an aqueous solvent. Preferably, glycidyl groups are hydrolyzed in an aqueous solvent using an acid catalyst such as sulfuric acid before or after the reaction for introducing amino groups, whereby prompt hydrolysis can be ensured. The hydrolysis temperature is usually 4° C. to 100° C., and preferably 20° C. to 80° C., and the reaction time is usually 5 minutes to 24 hours, and preferably 30 minutes to 12 hours.

As one example of magnetic particles obtained by the reaction of introducing amino groups, magnetic particles comprising a mother particle containing superparamagnetic particles, a hydrophobic first polymer layer formed on the surface of the mother particle, and a second polymer layer having an amino group and a 2,3-hydroxypropyl group formed on the first polymer layer can be given. The mother particle comprises a nuclear particle and a magnetic material layer comprising superparamagnetic particles formed on the surface of the nuclear particle, and the first polymer layer is formed on the magnetic material layer. When the second polymer layer contains an amino group and a 2,3-hydroxypropyl group, the magnetic particles have excellent capability of bonding with a probe and exhibit only small non-specific adsorption.

1.4.2. Reaction for Introducing Aldehyde Group (b) The reaction for introducing an aldehyde group is more specifically a reaction to produce an aldehyde group by converting the glycidyl groups contained in the second polymer layer into a group containing a diol group (a 2,3-hydroxypropyl group) by hydrolysis and by oxidatively cleaving a part of the diol group using an oxidizer. Magnetic particles having an aldehyde group introduced therein can be obtained by this reaction. The magnetic particles having an aldehyde group introduced therein can be suitably used for bonding a probe.

The conditions for hydrolyzing glycidyl groups are the same as those described in the description relating to the reaction of introducing amino groups in (a) above.

As the oxidizer suitable for converting a diol into aldehyde, known oxidizers such as periodic acid, periodate, and lead tetraacetate can be given. Among these, periodates such as sodium periodate and potassium periodate are preferable, because the reaction can be easily carried out in an aqueous solvent.

When an oxidizer suitable for use with an aqueous solvent such as periodate is used, the reaction for introducing an aldehyde group is carried out, for example, by hydrolyzing glycidyl groups, removing the supernatant liquid by washing and magnetic separation, and adding an aqueous solution of the oxidizer. When an oxidizer suitable for use with an organic solvent such as lead tetraacetate is used, the reaction for converting glycidyl groups into aldehyde groups is preferably carried out by hydrolyzing glycidyl groups, removing the supernatant liquid by washing and magnetic separation, drying the resulting particles, and dispersing the dried particles in the solution of the oxidizer. A preferable temperature of the reaction to introduces aldehyde groups and the reaction time vary according to the concentration of the glycidyl group in the second polymer layer, the degree of hydrolysis, the type of solvent, and the like. The reaction is carried out at a temperature usually from 4° C. to 100° C., preferably from 20° C. to 80° C., usually for 1 minute to 12 hours, and preferably for 10 minutes to 6 hours. It is not necessary that all glycidyl groups be converted into aldehyde groups in the reaction for introducing aldehyde groups.

The amount of the aldehyde groups in the magnetic particles according to this embodiment is preferably from 0.1 micromol/g to 100 micromol/g, and still more preferably from 0.5 micromol/g to 50 micromol/g. If the amount of the aldehyde groups is less than 0.1 micromol/g, the amount of probes that can bond to the magnetic particles is small, and signals emitted may be poor, and if more than 100 micromol/g, the non-specific adsorption may increase.

As one example of magnetic particles obtained by the reaction of introducing aldehyde groups, magnetic particles comprising a mother particle containing superparamagnetic particles, a hydrophobic first polymer layer formed on the surface of the mother particle, and a second polymer layer having an aldehyde group and a 2,3-hydroxypropyl group formed on the first polymer layer can be given. The mother particle comprises a nuclear particle and a magnetic material layer comprising superparamagnetic particles formed on the surface of the nuclear particle, and the first polymer layer is formed on the magnetic material layer. When the second polymer layer contains an aldehyde group and a 2,3-hydroxypropyl group, the magnetic particles have excellent capability of easily bonding with a probe containing an amino group by mixing with that probe and exhibit only a small non-specific adsorption.

1.4.3. Reaction for Introducing Carboxyl Group (c)-1. As the reaction for introducing carboxyl groups, (i) a reaction of acting a carboxylation agent (for example, a dicarboxylic acid, an aminocarboxylic acid, or an organic compound having three or more carboxyl groups in the molecule) on the glycidyl groups contained in the second polymer layer, (ii) a reaction of acting a carboxylation agent (for example, carboxylic acid anhydride, carboxylic acid chloride) on hydroxyl groups obtained by hydrolyzing the glycidyl groups contained in the second polymer layer, (iii) a reaction of acting an organic compound having two or more carboxyl groups in the molecule (for example, a dicarboxylic acid or an organic compound having three or more carboxyl groups in the molecule) on hydroxyl groups obtained by hydrolyzing the glycidyl groups contained in the second polymer layer in the presence of a suitable dehydrating catalyst, and the like can be given. Magnetic particles having carboxyl groups introduced therein can be obtained by these reactions. The magnetic particles having carboxyl groups introduced therein can be suitably used for bonding probes.

From the viewpoint of easy control of the amount of carboxyl groups introduced, the reaction (ii) is preferable. A reaction of acting a carboxylic acid anhydride as a carboxylation agent on hydroxyl groups (hydroxyl groups in 2,3-hydroxypropyl groups) obtained by hydrolyzing the glycidyl groups contained in the second polymer layer is particularly preferable. It is preferable to react a part of the 2,3-hydroxypropyl groups with the carboxylic acid anhydride. The carboxylic acid anhydride used herein is a polycarboxylic acid anhydride. Specific examples include aliphatic dicarboxylic acid anhydrides such as itaconic acid anhydride, succinic acid anhydride, citraconic acid anhydride, dodecenylsuccinic acid anhydride, tricarbanilic acid anhydride, glutaric acid anhydride, maleic acid anhydride, hexahydrophthalic acid anhydride, methyltetrahydrophthalic acid anhydride, and himic acid anhydride; alicyclic polyvalent carboxylic acid dianhydrides such as 1,2,3,4-butanetetracarboxylic acid dianhydride and cyclopentanetetracarboxylic acid dianhydride; and aromatic polyvalent carboxylic acid anhydrides such as phthalic acid anhydride, pyromellitic acid anhydride, trimellitic acid anhydride, and benzophenonetetracarboxylic acid anhydride. Among these, 1,2-dicarboxylic acid anhydrides such as succinic acid anhydride, maleic acid anhydride, and phthalic acid anhydride are preferred.

As a specific reaction for causing a carboxylic acid anhydride to act on hydroxyl groups obtained by hydrolyzing the glycidyl groups contained in the second polymer layer as a carboxylation agent, a method of dispersing a dry powder of hydrolyzed particles in an organic solvent in which the carboxylic acid anhydride is dissolved and stirring the mixture at a temperature from room temperature to 80° C. for 1 to 24 hours can be given. The organic solvent used here is not specifically limited. For example, pyridine, acetone, methyl ethyl ketone, tetrahydrofuran, and dimethylformamide can be given. As a catalyst, sulfuric acid, p-toluenesulfonic acid, zinc chloride, sodium acetate, pyridine, 4-dimethylaminopyridine, 4-pyrrolidinopyridine, or triethylamine may be used. Among these organic solvents and catalysts, pyridine which can act both as an organic solvent and a catalyst is suitable.

All hydroxyl groups on the magnetic particles according to this embodiment are not necessarily esterified, as it is preferable that some hydroxyl groups remain as is without being esterified.

In the case of the above-mentioned reactions (i) to (iii), it is preferable to hydrolyze a part of two or more glycidyl groups before the reaction of introducing carboxyl groups, or to hydrolyze a part of two or more glycidyl groups simultaneously with the reaction of introducing carboxyl groups. In addition, in the case of the reaction (i), it is possible to hydrolyze a part or all of the two or more glycidyl groups remaining after the reaction of introducing amino groups.

The amount of the carboxyl groups in the magnetic particles according to this embodiment is preferably from 0.1 micromol/g to 100 micromol/g, and more preferably from 0.5 micromol/g to 50 micromol/g. If the amount of the carboxyl groups is less than 0.1 micromol/g, the number of probes that can bond to the magnetic particles may be too small resulting in weak signals, and if more than 100 micromol/g, the non-specific adsorption may increase.

As one example of magnetic particles obtained by the reaction of introducing carboxyl groups, magnetic particles comprising a mother particle containing superparamagnetic particles, a hydrophobic first polymer layer formed on the surface of the mother particle, and a second polymer layer having a carboxyl group and a 2,3-hydroxypropyl group formed on the first polymer layer can be given. The mother particle comprises a nuclear particle and a magnetic material layer comprising superparamagnetic particles formed on the surface of the nuclear particle, and the first polymer layer is formed on the magnetic material layer. When the second polymer layer contains a carboxyl group and a 2,3-hydroxypropyl group, the magnetic particles exhibit only small non-specific adsorption. In addition, since the magnetic particles contain carboxyl groups which are widely handled in the biochemical field, magnetic particles can be used to advantage by applying knowledge in this field.

1.4.4. Reaction for Converting Carboxyl Group into Active Ester Group (c)-2. After introducing carboxyl groups, as the reaction for converting the carboxyl groups into active ester groups, a method of introducing the active ester groups by chemically modifying the magnetic particles into which the carboxyl groups have been introduced by the above reaction for introducing carboxyl groups using a suitable activator can be given, for example. Magnetic particles having active ester groups introduced therein can be obtained by these reactions. The magnetic particles having active ester groups introduced therein can be suitably used for bonding probes. As a suitable activator, N-hydroxysuccinimide and N-hydroxysulfosuccinimide can be given. There are no specific limitations to the active esters. An N-succinimidyloxycarbonyl group and an N-sulfosuccinimidyloxycarbonyl group can be given as examples.

As a specific method for introducing active ester groups, for example, a method of adding 1-ethyl-3-(3-dimethylaminopropyl)carbodiimide hydrochloride and N-hydroxysuccinimide to an aqueous dispersion of magnetic particles with carboxyl groups introduced therein, and heating the mixture at a temperature from room temperature to 80° C. for 1 to 24 hours can be given.

The amount of the active ester groups in the magnetic particles according to this embodiment is preferably from 0.1 micromol/g to 100 micromol/g, and more preferably from 0.5 micromol/g to 50 micromol/g. If the amount of the active ester groups is less than 0.1 micromol/g, the number of probes that can bond to the magnetic particles may be too small, which may result in magnetic particles emitting only weak signals. If more than 100 micromol/g, the non-specific adsorption may increase.

As one example of magnetic particles obtained by the reaction of introducing active ester groups, magnetic particles comprising a mother particle containing superparamagnetic particles, a hydrophobic first polymer layer formed on the surface of the mother particle, and a second polymer layer having an active ester group and a 2,3-hydroxypropyl group formed on the first polymer layer can be given. The mother particle comprises a nuclear particle and a magnetic material layer comprising superparamagnetic particles formed on the surface of the nuclear particle, and the first polymer layer is formed on the magnetic material layer. When the second polymer layer contains an active ester group and a 2,3-hydroxypropyl group, the magnetic particles have excellent capability of easily bonding with a probe containing an amino group by mixing with that probe, the probe is released from the magnetic particles only with difficulty, and the magnetic particles exhibit only small non-specific adsorption.

1.5. Diameter of Particles and Method of Use

The average particle diameter of the nuclear particles according to this embodiment is preferably from 0.4 to 200 micrometers, more preferably from 0.8 to 100 micrometers, and most preferably from 1.0 to 50 micrometers. If the average particle diameter of the nuclear particles is less than 0.4 micrometers, magnetic separation properties may be poor. On the other hand, if the average particle diameter is more than 200 micrometers, gravity precipitation is remarkable, which may provide probe-bonded particles with a non-uniform reaction field.

The magnetic particles according to this embodiment are used in the form of an aqueous dispersion or a dry powder. The aqueous dispersion can be obtained usually by washing the magnetic particles with an aqueous solvent such as distilled water after chemically modifying the glycidyl groups, adding an aqueous solvent, and stirring, homogenizing, or ultrasonically treating the mixture. A dry powder can be obtained by drying the aqueous dispersion with heating, vacuum drying, spray drying, freeze drying, or the like.

2. Use

The magnetic particles according to this embodiment can be conveniently used as particles for probe bonding. More specifically, the particles can be used as particles for compound carriers and affinity carriers such as particles for chemical bonding carriers for diagnostics. In particular, the magnetic particles exhibit outstandingly high sensitivity and low noise when used as probe-bonded magnetic particles used for immunoassay and proteome assay in which primary probes such as an antigen or an antibody is bonded.

In the magnetic particles for probe bonding according to this embodiment, the substances to be inspected are biological-related substances, chemical compounds, and living organisms contained in the reagent for immunological assay and test samples. In the invention, "biological-related substances" refer to all substances related to living organisms. As examples of the biological-related substances, substances contained in living organisms, substances derived from living organisms, and substances which can be used in living organisms can be given.

The biological-related substances include, but are not limited to, for example, proteins (for example, enzymes, antibodies, aptamers, acceptors), peptides (for example, glutathione), nucleic acids (for example, DNA, RNA), carbohydrates, lipids, hormones (for example, luteinizing hormone, human chorionic gonadotropin, thyroid stimulating hormone, insulin, glucagon, growth hormone), and other cells or substances (for example, various blood origin substances including various blood cells such as platelets, erythrocytes, and leukocytes, various floating cells, and proteins and nucleic acids which are constituents of viruses, bacteria, fungi, protozoans, and parasites). As more specific examples of the proteins, proteins of biological origin, prostate specific markers, and various cancer markers such as a bladder cancer marker can be given.

Chemical compounds to be inspected are not particularly limited and include, for example, environmental pollutants such as dioxins and medical supplies such as antibiotics, anticancer drugs, and antiepileptic drugs.

The living organisms to be inspected are not particularly limited and include, for example, various cancer cells, various floating cells, viruses (for example, hepatitis B virus, hepatitis C virus, simple herpesvirus, HIV viruses, German measles virus, and influenza virus), bacteria (for example, gonococci, MRSA, and *Escherichia coli*), fungi (for example, *Candida, Trichophyton, Cryptococcus*, and *Aspergillus*), protozoan and parasites (for example, *toxoplasma* and malaria).

If the aldehyde group-introduced particles and active ester group-introduced particles among the magnetic particles for probe bonding according to this embodiment are used, probes can be chemically bonded to the surface of the particles by simply mixing the probes with these particles when actually used.

If the amino group-introduced particles or carboxyl group-introduced particles are used among the magnetic particles for probe bonding according to this embodiment, since the amino groups or carboxyl groups are already introduced onto the surface of particles, probes can be chemically bonded to the surface of these particles by activating the probes or the carboxyl groups of the particles using a known water-soluble activating agent such as carbodiimide and mixing the probes with these particles when actually used.

After bonding the probes to the surface of these particles, excessive probes are washed out and unreacted active groups are inactivated, as required. As an inactivation agent, a compound containing a hydroxyl group such as ethanolamine and tris(hydroxymethylamino)methane is preferably used. Although a commonly practiced blocking operation is unnecessary after bonding the probes to the surface of these particles, it is possible to use a blocking agent such as albumin, skim milk, and casein during inactivation. After that, a common process using particles may be carried out.

Probes which can be carried on the magnetic particles for probe bonding according to this embodiment are proteins (antigens and antibodies), nucleic acids, and compounds. Of these, antigens and antibodies are preferably used. In this case, the antigens and antibodies are not specifically limited insofar as the antigens and antibodies are reactive with components commonly contained in test samples. Such antigens and antibodies include, but are not limited to, antigens and antibodies for coagulate fibrinolytic-related inspection such as an anti-antiplasmin antibody for anti plasmin inspection, an anti-D-dimer antibody for D-dimer inspection, an anti-FDP antibody for FDP inspection, an anti-tPA antibody for tPA inspection, an anti-thorombin=antithrombin complex antibody for TAT inspection, and an anti-FPA antibody for FPA inspection; antigens and antibodies for tumor-related inspection such as an anti-BFP antibody for BFP inspection, an anti-CEA antibody for CEA inspection, an anti-AFP antibody for AFP inspection, an anti-ferritin antibody for ferritin inspection, and an anti-CA19-9 antibody for CA19-9 inspection; and antigens and antibodies for blood-serum protein-related inspection such as an anti-apolipoprotein antibody for apolipoprotein inspection, an anti-beta2-microblobulin for beta2-microblobulin inspection, an anti-alpha1-microglobulin for microglobulin inspection, an anti-immunoglobulin antibody for immunoglobulin inspection, and an anti-CRP antibody for CRP inspection; antigens and antibodies for inspecting endocrine functions such as an anti-HCG antibody for HCG inspection; antigens and antibodies for infection-related inspection such as an anti-HBs antibody for HBs antibody inspection, an HBs antigen for HBs antibody inspection, an HCV antigen for HCV antibody inspection, an HIV-1 antigen for HIV-1 antibodies, an HIV-2 antigen for HIV-2 antibody inspection, an HTLV-1 antigen for HTLV-1 inspection, a mycoplasma antigen for mycoplasma disease inspection, a *toxoplasma* antigen for *toxoplasma* inspection, and a streptolysin O antigen for ASO inspection; antigens or antibodies for an autoimmune-related inspection such as a DNA antigen for anti-DNA antibody inspection and thermally-modified human IgG for RF inspection; and antigens and antibodies for drug analysis such as an anti-digoxin antibody for digoxin inspection and anti-lidocaine antibody for lidocaine inspection. Either a polyclonal antibody or a monoclonal antibody can be used as an antibody.

Moreover, the magnetic particles for probe bonding according to this embodiment can also be used as an affinity carrier of which the particle surface is sensitized with proteins such as enzymes and hormones, nucleic acids such as DNA-RNA, lipids, or physiologically active sugar chain compounds. Furthermore, it is possible to select and purify a protein (a target molecule) specifically reacting with the chemical compound to be analyzed (corresponding to a ligand molecule) by chemically bonding and immobilizing the chemical compound to be analyzed to the magnetic particles for probe bonding according to this embodiment and analyzing and/or measuring the specific interaction with the protein.

The ligand molecule bonded to the particles is not specifically limited insofar as the ligand molecule has a functional group reactive with at least one functional group possessed by the magnetic particles for probe bonding according to this embodiment. Examples include nucleic acids, peptide nucleic acids, hormones, proteins with a molecular weight of 500 to 1,000,000, sugar chains, polysaccharides, cells, aptamers, viruses, enzymes, various tag capture substances for affinity, coenzymes such as biotin, and chemical compounds which have or may have a specific physiologically active effect.

3. EXAMPLES

The invention is described below in more detail by way of examples. It should be understood that the invention is not limited to the following examples. Various evaluations in the following examples and comparative examples were carried out by the following methods.

3.1. Evaluation Method 3.1.1. Nuclear Particles

The number average particle diameter measured by a laser diffraction particle size distribution measuring device (SALD-200V™ manufactured by Shimadzu Corp.) was regarded as the average particle diameter of the particles.

3.1.2. Non-specific Adsorption and Sensitivity

The non-specific adsorption and sensitivity of magnetic particles for probe bonding were evaluated according to the following methods. 100 microliters of a 1 wt % dispersion of the magnetic particles for probe bonding was sampled in a tube. Particles were magnetically separated to remove the supernatant liquid. 500 microliters of a Jurkat cell crush solution which is confirmed to contain the target protein (20S proteasome) was added to the particles. The mixture was vibrated by a touch mixer to disperse the particles in the solution, followed by mixing by rotation and inversion for two hours at room temperature. After magnetic separation, the supernatant liquid was removed. 1 ml of a 10 mM HEPES containing 0.05% of a nonionic surfactant NP40 was added and the particles were dispersed using a touch mixer. After further repeating the same procedure twice, the content was transferred to a new tube to perform magnetic separation, and the supernatant liquid was removed. After the addition of 50 microliters of a 0.5% aqueous solution of sodium dodecyl-sulfate, the mixture was gently vibrated to disperse the particles. After allowing the mixture to stand for 10 minutes, the magnetic separation was performed and 20 microliters of a supernatant liquid was collected. 2-Mercaptoethanol was dissolved in a premix sample buffer solution manufactured by Bio-Rad Laboratories, Inc. to a concentration of 2 wt %. 20 microliters of the solution was collected in the tube. 20 microliters of the supernatant liquid collected in the above process was mixed and heated at 100° C. for 5 minutes in a tube heater. The mixture was applied to a vertical electrophoresis system (Mini-PROTEAN3™ manufactured by Bio-Rad Laboratories, Inc.) in an amount of 20 microliters per one lane to perform electrophoresis using a precast polyacrylamide gel (Ready Gel J™ (15%) manufactured by Bio-Rad Laboratories, Inc.) and a premix electrophoresis buffer solution manufactured by Bio-Rad Laboratories, Inc. The gel was stained by a standard staining method using Silver Stain Plus Kit™ manufactured by Bio-Rad Laboratories, Inc. An image was produced by scanning the stained gel using a densitometer GS-700™ manufactured by Bio-Rad Laboratories, Inc. Samples in which the several bands near the molecular weight of 31 k corresponding to a protein which constitutes a subunit of 20S proteasome were clearly identified were regarded to have good sensitivity and rated as "Good", otherwise the samples were rated as "Bad". Samples in which almost no bands other than the bands near the molecular weight of 31 k were identified were regarded to have low non-specific adsorption and rated as "Good", otherwise the samples were rated as "Bad".

3.2. Synthesis Example

3.2.1. Production of Nuclear Particles 2 parts by mass of a 75% di(3,5,5-trimethylhexanoyl) peroxide solution (PEROYL 355-75(S)™ manufactured by NOF Corp. (hereinafter referred to as "Peroyl")) was mixed with 20 parts by mass of a 1% sodium dodecylsulfate aqueous solution. The mixture was processed by an ultrasonic disperser to obtain a fine emulsion. The emulsion was added to a reactor containing 13 parts by mass of polystyrene particles with a particle diameter of 0.77 micrometer and 41 parts by mass of water. The mixture was stirred at 25° C. for 12 hours. In another vessel, 95 parts by mass of methyl methacrylate (hereinafter referred to as "MMA"), 5 parts by mass of trimethylolpropane trimethacrylate (hereinafter referred to as "TMP"), and 400 parts by mass of a 0.1% sodium dodecylsulfate aqueous solution were mixed and emulsified. The emulsion was added to the above reactor and the mixture was stirred at 40° C. for 2 hours, heated to 75° C., and polymerized for 8 hours. After cooling to room temperature, the particles were collected by centrifugation, washed with water, dried, and pulverized to obtain "nuclear particles A-1" having a diameter of 1.5 micrometers.

3.2.2. Production of Mother Particles (Formation of Magnetic Material Layer)

Acetone was added to an oily magnetic fluid (EXP series™ manufactured by Ferrotec Corporation) to cause particles to deposit as a precipitate. The precipitate was dried to obtain superparamagnetic particles of ferrite having a hydrophobized surface (average diameter of primary particles: 0.01 micrometers).

15 g of the nuclear particles A-1 and 20 g of the hydrophobized superparamagnetic particles were sufficiently mixed using a mixer. The mixture was processed by a hybridization system (NHS-0-Type™ manufactured by Nara Machinery Co., Ltd.) at a stirring blade peripheral velocity of 100 m/sec (16,200 rpm) for 5 minutes to obtain mother particles A-2 of superparamagnetic particles having a magnetic material layer on the surface (particle diameter: 1.7 micrometers).

3.2.3. Formation of First and Second Layers on Mother Particles

A 1 liter separable flask was charged with 375 g of a 0.5 wt % of sodium dodecylbenzenesulfonate aqueous solution. 15 g of the mother particles A-2 was added and dispersed using a homogenizer, and the resulting dispersion was heated to 60° C. In another vessel, 18 g of MMA, 2 g of TMP, and 0.4 g of Peroyl were dispersed in 100 g of a 0.5 wt % sodium dodecylsulfate aqueous solution to obtain a preemulsion, which was added dropwise to the above 1 liter separable flask in one and a half hours while controlling the temperature at 60° C. (formation of the first polymer layer).

After the addition, the mixture was stirred for one hour while controlling the temperature at 60° C. Then, another lot of preemulsion prepared by dispersing 10.5 g of glycidyl methacrylate, 1.5 g of TMP, and 0.3 g of Peroyl in 75 g of a 0.5 wt % sodium dodecylsulfate aqueous solution was added dropwise to the above 1 liter separable flask in one and a half hours while controlling the temperature at 60° C. The temperature was increased to 75° C. to continue the polymerization for two hours (formation of second polymer layer).

The particles in the separable flask were separated using magnetism and washed with distilled water, thereby obtaining magnetic particles A-3 (diameter: 2.7 micrometers) with a second polymer layer having glycidyl groups formed thereon.

3.3. Example 1

Preparation of Amino Group-introduced Magnetic Particles for Probe Bonding and Evaluation of Probe-bonded Magnetic Particles The particles obtained from the magnetic particles A-3 with a second polymer layer having glycidyl groups formed thereon by magnetic separation were dispersed in acetone. After repeating a procedure of separating the particles by magnetism and washing the separated particles with acetone five times, the particles were again dispersed in acetone and the supernatant liquid was removed by magnetic separation. The particles obtained were dried. 0.50 g of the particles were put into a 100 ml flask and 25 g of ethylenediamine was added. The particles were dispersed by indirect ultrasonic radiation for 20 minutes. The dispersion liquid was stirred at 50° C. in a nitrogen atmosphere for 3 hours (introduction of amino groups).

After cooling, the particles were separated by magnetic separation and dispersed in distilled water. A procedure of magnetic separation and washing was repeated five times. After removing a supernatant liquid by magnetic separation, 5 g of a 1% aqueous solution of sulfuric acid was added to the particles. The particles were dispersed by indirect ultrasonic radiation for 20 minutes. The dispersion liquid was stirred at 60° C. for 5 hours (hydrolysis of residual glycidyl groups).

The particles were separated by magnetic separation and dispersed in purified water. A procedure of dispersing in purified water, separating by magnetic separation, and washing was repeated five times to obtain 0.49 g of amino group-introduced magnetic particles Am-1.

The amino group-introduced magnetic particles Am-1 were diluted with and dispersed in purified water to obtain a water dispersion with a particle concentration of 1 wt %. 500 microliters of the water dispersion was put into a tube to separate the magnetic particles and remove the supernatant liquid using a magnetic stand. After washing three times with a 50 mM MES-NaOH buffer solution (pH 6, hereinafter referred to as "Buffer-1"), the particles were dispersed in 500 microliters of Buffer-1. After the addition of 0.05 mg of a protein (anti-20S proteasome alpha6•mouse IgG antibody) used as the probe for specifically catching 20S proteasome which is the target substance, and further addition of 0.25 mg of 1-ethyl-3-(3-dimethylaminopropyl)carbodiimide (EDC), the mixture was stirred at room temperature for two hours. After the reaction, the particles were separated by magnetic separation and the supernatant liquid was removed. Then, 500 microliters of a PBS (−) buffer solution was added and the mixture was stirred at room temperature for two hours. Furthermore, after washing five times with a PBS (−) buffer solution, the particles were dispersed in 500 microliters of PBS (−) buffer solution to obtain a dispersion liquid of probe (antibody)-bonded magnetic particles.

A stained gel image of electrophoresis is shown in FIG. 1. As shown in FIG. 1, the non-specific adsorption and sensitivity of the probe-bonded particles obtained in this Example were evaluated as "Good".

3.4. Example 2

Preparation of Aldehyde Group-introduced Magnetic Particles for Probe Bonding and Evaluation of Probe-bonded Magnetic Particles 5 g of a 1% aqueous solution of sulfuric acid was added to 0.5 g of particles separated by magnetic separation from a water dispersion of magnetic particles A-3 with a second polymer layer having glycidyl groups formed thereon. The particles were dispersed by indirect ultrasonic radiation for 20 minutes and the dispersion liquid was stirred at 60° C. for 5 hours (hydrolysis of glycidyl groups).

The particles were separated by magnetic separation and dispersed in purified water. A procedure of magnetic separation and washing was repeated five times. 20 ml of a 5.6 mg/ml aqueous solution of sodium periodate was added to the particles obtained by magnetic separation and the mixture was reacted at room temperature for one hour while stirring (introduction of aldehyde groups).

The particles were separated by magnetic separation and the amount of formaldehyde in the supernatant was analyzed using Glycoprotein Carbohydrate Estimation Kit™ (manufactured by Pierce Biotechnology, Inc.) to confirm that 11 micromol of aldehyde group was introduced per 1 g of particles. The particles were dispersed in distilled water, and a procedure of magnetic separation, followed by washing was repeated five times. Finally, the particles were dispersed in distilled water to obtain a 1% dispersion liquid containing 0.49 g of aldehyde group-introduced magnetic particles AL-1.

500 microliters of the 1 wt % dispersion liquid of the aldehyde group-introduced magnetic particles AL-1 was put into a tube to separate the magnetic particles and remove the supernatant liquid using a magnetic stand. After washing three times with a citrate-carbinate buffer solution (pH 10, hereinafter referred to as "Buffer-2"), the particles were dispersed in 500 microliters of Buffer-2. After the addition of 0.05 mg of a protein (anti-20S proteasome alpha6•mouse IgG antibody) used as the probe for specifically catching 20S proteasome which is the target substance, the mixture was stirred at room temperature for five hours. After the reaction, the particles were separated by magnetic separation and the supernatant liquid was removed. Then, 500 microliters of a tris-HCl buffer solution (pH 7.4) was added and the mixture was stirred at room temperature for two hours. Furthermore, after washing five times with a PBS (−) buffer solution, the particles were dispersed in 500 microliters of PBS (−) buffer solution to obtain a dispersion liquid of probe (antibody)-bonded magnetic particles.

A stained gel image of electrophoresis is shown in FIG. 1. As shown in FIG. 1, the non-specific adsorption and sensitivity of probe-bonded particles obtained in this Example were evaluated as "Good".

3.5. Example 3

Preparation of Carboxyl Group-introduced Magnetic Particles for Probe Bonding and Evaluation of Probe-bonded Magnetic Particles 10 g of a 1% aqueous solution of sulfuric acid was added to 1.0 g of particles separated from a water dispersion of magnetic particles A-3 with a second polymer layer having glycidyl groups formed thereon by magnetic separation. The particles were dispersed by indirect ultrasonic radiation for 20 minutes and the dispersion liquid was stirred at 60° C. for five hours (hydrolysis of glycidyl groups).

The particles were separated by magnetic separation, dispersed in purified water. A procedure of dispersing in purified water, separating by magnetism, and washing was repeated five times. The particles were dried. 1.0 g of the resulting dry particles was washed with 10 ml of pyridine, dispersed in 5 ml of pyridine, added to a solution of 3 g of succinic acid anhydride dissolved in 25 ml of pyridine. The mixture was stirred at 60° C. for two hours (introduction of carboxyl group).

After the reaction, the particles were separated using magnetism, washed three times with acetone, three times with a 0.1M sodium hydroxide aqueous solution, and four times with distilled water, and dispersed in distilled water to obtain 1.0 g of a 1% dispersion liquid containing 1.0 g of carboxyl group-introduced magnetic particles Ca-1.

500 microliters of the 1 wt % dispersion liquid of the carboxyl group-introduced magnetic particles Ca-1 was put into a tube to separate the magnetic particles and remove the supernatant liquid using a magnetic stand. After washing three times with Buffer-1, the particles were dispersed in 500 microliter of Buffer-1. After the addition of 0.05 mg of a protein (anti-20S proteasome alpha6•mouse IgG antibody) used as the probe for specifically catching 20S proteasome which is the target substance, and further addition of 0.25 mg of EDC, the mixture was stirred at room temperature for two hours. After the reaction, the particles were separated by magnetic separation and the supernatant liquid was removed. Then, 500 microliters of a PBS (−) buffer solution was added and the mixture was stirred at room temperature for two hours. Furthermore, after washing five times with a PBS (−) buffer solution, the particles were dispersed in 500 microliters of PBS (−) buffer solution to obtain a dispersion liquid of probe (antibody)-bonded magnetic particles.

A stained gel image of electrophoresis is shown in FIG. 1. As shown in FIG. 1, the non-specific adsorption and sensitivity of probe-bonded particles obtained in this Example were evaluated as "Good".

3.6. Example 4

Preparation of Active Ester Group-introduced Magnetic Particles for Probe Bonding and Evaluation of Probe-bonded Magnetic Particles 100 ml of the 1% dispersion liquid of the carboxyl group-introduced magnetic particles Ca-1 obtained in Example 3 was put into a beaker to separate the magnetic particles and remove the supernatant liquid by magnetization. After washing three times with Buffer-1, the particles were dispersed in 100 ml of Buffer-1. 0.16 g of N-hydroxysuccinic acid imide and 0.18 g of EDC were added and the mixture was stirred at room temperature for two hours (introduction of active ester group).

After the reaction, a procedure of magnetic separation, dispersion, and washing was repeated five times. Finally, the particles were dispersed in distilled water to obtain a 1% dispersion liquid containing 1.0 g of active ester group-introduced magnetic particles Ac-1.

500 microliters of the 1 wt % dispersion liquid of the active ester group-introduced magnetic particles Ac-1 was put into a tube to separate the magnetic particles and remove the supernatant liquid using a magnetic stand. After washing three times with 50 mM MES-NaOH (pH 6, Buffer-1), the particles were dispersed in 500 microliters of Buffer-1. After the addition of 0.05 mg of a protein (anti-20S proteasome alpha6•mouse IgG antibody) used as the probe for specifically catching 20S proteasome which is the target substance, the mixture was stirred at room temperature for two hours. After the reaction, the particles were separated by magnetic separation and the supernatant liquid was removed. Then, 500 microliters of a PBS (−) buffer solution was added and the mixture was stirred at room temperature for two hours. Furthermore, after washing five times with a PBS (−) buffer solution, the particles were dispersed in 500 microliters of PBS (−) buffer solution to obtain a dispersion liquid of probe (antibody)-bonded magnetic particles.

A stained gel image of electrophoresis is shown in FIG. 1. As shown in FIG. 1, the non-specific adsorption and sensitivity of probe-bonded particles obtained in this Example were evaluated as "Good".

3.7. Comparative Example 1

Example not Containing Chemical Modification of Glycidyl Group

The magnetic particles A-3 with a glycidyl group-containing second polymer layer formed thereon were diluted with and dispersed in purified water to obtain a water dispersion liquid with a particle concentration of 1 wt %. 500 microliters of the water dispersion was put into a tube to separate the magnetic particles and remove the supernatant liquid using a magnetic stand. After washing three times with 500 microliters of Buffer-1, the particles were dispersed in 500 microliters of Buffer-1. 0.05 mg of a protein (anti-20S proteasome alpha6•mouse IgG antibody) used as the probe for specifically catching 20S proteasome which is the target substance was added and the mixture was stirred at room temperature for two hours. After the reaction, the particles were separated by magnetic separation and the supernatant liquid was removed. Then, 500 microliters of a PBS (−) buffer solution was added and the mixture was stirred at room temperature for two hours. Furthermore, after washing five times with a PBS (−) buffer solution, the particles were dispersed in 500 microliters of PBS (−) buffer solution to obtain a dispersion liquid of probe (antibody)-bonded magnetic particles.

A stained gel image of electrophoresis is shown in FIG. 1. As shown in FIG. 1, the probe-bonded particles obtained in this Comparative Example were evaluated to have "Bad" sensitivity and "Good" non-specific adsorption.

3.8. Comparative Example 2

Commercial Agarose Gel 20 microliter of an extract obtained from a commercially-available 20S proteasome capture kit containing agarose gel as a carrier (Proteasome Isolation Kit, Human, manufactured by Merck Co.) was sampled in a tube to evaluate the non-specific adsorption and sensitivity. A stained gel image of electrophoresis is shown in FIG. 1. The sensitivity was "Bad" and the non-specific adsorption was "Good" when the agarose gel used in this Comparative Example was used as a carrier in the 20S proteasome capture kit.

3.9. Comparative Example 3

Example without the First Polymer Layer

Carboxyl group-introduced magnetic particles Ca-2 were obtained in the same manner as in Example 3, except for using magnetic particles B on which no first polymer layer is provided, but only a second polymer layer having a glycidyl group is provided, instead of the magnetic particles A-3 with a glycidyl group-containing second polymer layer formed thereon. Probe-bonded magnetic particles were formed in the same manner as in Example 3 using these carboxyl group-introduced magnetic particles Ca-2, and the non-specific adsorption and sensitivity of the probe-bonded magnetic particles were evaluated. A stained gel image of electrophoresis is shown in FIG. 1. As shown in FIG. 1, the probe-bonded particles obtained in this Comparative Example were evaluated to have "Bad" sensitivity and "Bad" non-specific adsorption.

Although only some embodiments of the invention have been described in detail above, those skilled in the art would readily appreciate that many modifications are possible in the embodiments without materially departing from the novel teachings and advantages of the invention. Accordingly, such modifications are intended to be included within the scope of the invention.

What is claimed is:

1. A magnetic particle comprising:
   a mother particle containing superparamagnetic particles;
   a hydrophobic first polymer layer formed on the surface of the mother particle; and
   a second polymer layer having an amino group and a 2,3-hydroxypropyl group formed on the first polymer layer.

2. The magnetic particle according to claim 1,
   wherein the mother particle comprises a nuclear particle and a magnetic material layer containing the superparamagnetic particles formed on the surface of the nuclear particle; and
   wherein the first polymer layer is formed on the magnetic material layer.

3. The magnetic particle according to claim 1, which is used for probe bonding.

4. A probe-bonded particle comprising the magnetic particle according to claim 1, and a probe bonded to the magnetic particle.

5. A magnetic particle comprising:
   a mother particle containing superparamagnetic particles;
   a hydrophobic first polymer layer formed on the surface of the mother particle; and
   a second polymer layer having an aldehyde group and a 2,3-hydroxypropyl group formed on the first polymer layer.

6. The magnetic particle according to claim 5,
   wherein the mother particle comprises a nuclear particle and a magnetic material layer containing the superparamagnetic particles formed on the surface of the nuclear particle; and
   wherein the first polymer layer is formed on the magnetic material layer.

7. The magnetic particle according to claim 5, which is used for probe bonding.

8. A probe-bonded particle comprising the magnetic particle according to claim 5, and a probe bonded to the magnetic particle.

9. A magnetic particle comprising:
   a mother particle containing superparamagnetic particles;
   a hydrophobic first polymer layer formed on the surface of the mother particle; and
   a second polymer layer having a carboxyl group and a 2,3-hydroxypropyl group formed on the first polymer layer.

10. The magnetic particle according to claim 9, wherein the mother particle comprises a nuclear particle and a magnetic material layer containing the superparamagnetic particles formed on the surface of the nuclear particle; and wherein the first polymer layer is formed on the magnetic material layer.

11. The magnetic particle according to claim 9, which is used for probe bonding.

12. A probe-bonded particle comprising the magnetic particle according to claim 9, and a probe bonded to the magnetic particle.

13. A magnetic particle comprising:
   a mother particle containing superparamagnetic particles;
   a hydrophobic first polymer layer formed on the surface of the mother particle; and
   a second polymer layer having an active ester group and a 2,3-hydroxypropyl group formed on the first polymer layer.

14. The magnetic particle according to claim 13,
   wherein the mother particle comprises a nuclear particle and a magnetic material layer containing the superparamagnetic particles formed on the surface of the nuclear particle; and
   wherein the first polymer layer is formed on the magnetic material layer.

15. The magnetic particle according to claim 13, which is used for probe bonding.

16. A probe-bonded particle comprising the magnetic particle according to claim 13, and a probe bonded to the magnetic particle.

* * * * *